(12) United States Patent
Thomas et al.

(10) Patent No.: US 7,612,001 B2
(45) Date of Patent: Nov. 3, 2009

(54) HIGH PERFORMANCE ELASTIC MATERIALS MADE USING STYRENE BLOCK COPOLYMERS AND MIXTURES

(75) Inventors: Oomman Painummoottil Thomas, Alpharetta, GA (US); Melpo Lambidonis, Cumming, GA (US); Ali Yahiaoui, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 163 days.

(21) Appl. No.: 11/024,927

(22) Filed: Dec. 22, 2004

(65) Prior Publication Data

US 2006/0135024 A1 Jun. 22, 2006

(51) Int. Cl.
*B32B 27/12* (2006.01)
*B32B 27/32* (2006.01)

(52) U.S. Cl. .................... 442/394; 442/398; 442/399; 428/424.8

(58) Field of Classification Search ............... 442/394, 442/398, 399
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,340,563 A | 7/1982 | Appel et al. | |
| 4,652,487 A | 3/1987 | Morman | |
| 4,655,760 A | 4/1987 | Morman et al. | |
| 4,657,802 A | 4/1987 | Morman | |
| 4,720,415 A | 1/1988 | Vander Wielen et al. | |
| 4,781,966 A | 11/1988 | Taylor | |
| 4,789,699 A | 12/1988 | Kieffer et al. | |
| 4,816,094 A | 3/1989 | Pomplun et al. | |
| 4,965,122 A | 10/1990 | Morman | |
| 4,981,747 A | 1/1991 | Morman | |
| 5,011,733 A | 4/1991 | Hiraki et al. | |
| 5,226,992 A | 7/1993 | Morman | |
| 5,332,613 A | 7/1994 | Taylor et al. | |
| 5,336,545 A | 8/1994 | Morman | |

(Continued)

FOREIGN PATENT DOCUMENTS

EP 0 733 472 A2 9/1996

(Continued)

OTHER PUBLICATIONS

*Steady Flow and Dynamic Viscosity of Branched Butadiene-Styrene Block Copolymers*, Kraus et al., Journal of Polymer Science: Part A-2, vol. 9, 1971, pp. 1839-1850.

*Primary Examiner*—Lynda Salvatore
(74) *Attorney, Agent, or Firm*—Dority & Manning, P.A.

(57) ABSTRACT

An elastic laminate having improved elastomeric properties is prepared by forming an elastic layer from a thermoplastic styrene block copolymer elastomer, crosslinking the elastic layer, and bonding the elastic layer to at least one nonwoven web. The elastic layer may be crosslinked before or after it is bonded to the nonwoven web. The elastic laminate combines the advantages of relatively low cost starting materials with the performance advantages typically associated with more expensive elastomers.

31 Claims, 2 Drawing Sheets

U.S. PATENT DOCUMENTS

| | | | |
|---|---|---|---|
| 5,385,775 | A | 1/1995 | Wright |
| 5,472,775 | A | 12/1995 | Obijeski et al. |
| 5,514,470 | A | 5/1996 | Haffner et al. |
| 5,789,065 | A | 8/1998 | Haffner et al. |
| 5,853,881 | A | 12/1998 | Estey et al. |
| 6,001,460 | A | 12/1999 | Morman et al. |
| 6,242,504 | B1 | 6/2001 | Meyer-Roscher et al. |
| 6,323,389 | B1 | 11/2001 | Thomas et al. |
| 6,342,565 | B1 * | 1/2002 | Cheng et al. ............... 525/191 |
| 6,387,471 | B1 | 5/2002 | Taylor et al. |
| 6,437,014 | B1 * | 8/2002 | Ho et al. .................... 522/75 |
| 6,555,624 | B2 | 4/2003 | Nishihara et al. |
| 6,570,714 | B2 | 5/2003 | Soane et al. |
| 6,767,852 | B2 | 7/2004 | Friderich et al. |
| 6,777,082 | B2 | 8/2004 | Patel et al. |
| 6,783,842 | B2 | 8/2004 | Niepelt |
| 6,794,024 | B1 | 9/2004 | Walton et al. |
| 6,808,789 | B2 | 10/2004 | Pelkie et al. |
| 2002/0019616 | A1 | 2/2002 | Thomas |
| 2002/0064653 | A1 | 5/2002 | Ladika et al. |
| 2003/0022582 | A1 * | 1/2003 | Cree et al. ................ 442/394 |
| 2003/0124331 | A1 | 7/2003 | Morell et al. |
| 2004/0005832 | A1 | 1/2004 | Neculescu et al. |
| 2004/0123938 | A1 | 7/2004 | Neculescu et al. |
| 2004/0170852 | A1 * | 9/2004 | Gustafson ................. 428/500 |
| 2004/0197588 | A1 | 10/2004 | Thomas et al. |
| 2005/0163960 | A1 | 7/2005 | Lapin |
| 2006/0055089 | A1 | 3/2006 | Zhang et al. |

FOREIGN PATENT DOCUMENTS

| | | |
|---|---|---|
| EP | 1331090 | 1/2003 |
| EP | 1 246 881 B1 | 4/2004 |
| FR | 2 802 849 A1 | 6/2001 |
| JP | 02255739 * | 10/1990 |

* cited by examiner

HIGH PERFORMANCE ELASTIC MATERIALS MADE USING STYRENE BLOCK COPOLYMERS AND MIXTURES

BACKGROUND OF THE INVENTION

Various elastic composites have been formed by bonding an elastic polymer layer in the form of a film, foam, nonwoven web or parallel strands, to one or more nonwoven facing layers. A "stretch bonded laminate" ("SBL") is any laminate in which an elastic layer is bonded to one or more facing layers while the elastic layer is stretched. When the elastic layer is subsequently relaxed, gathers form in the facing layer(s). Stretch-bonded laminates are described, for instance, in U.S. Pat. No. 6,387,471 to Taylor et al., and U.S. Pat. No. 6,323,389 to Thomas et al., which are incorporated herein by reference. A "neck-bonded laminate" ("NBL") is any laminate where an elastic layer is bonded to one or two non-elastic facing layers while the elastic layer is relaxed and the facing layer(s) are extended or necked to reduce their dimensions in the direction orthogonal to the extension. Neck-bonded laminates have cross-directional stretch and recovery properties. Neck-bonded laminates are described, for instance, in U.S. Pat. No. 5,853,881 to Estey et al., U.S. Pat. No. 4,965,122 to Morman, and U.S. Pat. No. 6,001,460 to Morman et al., and U.S. Pat. No. 5,789,065 to Haffner et al., which are incorporated herein by reference. A "neck-stretch bonded laminate" ("NSBL") is any laminate where an elastic layer is bonded to one or two facing layers while the elastic layer is stretched, and the facing layer(s) are extended in the same direction to cause necking in the direction orthogonal to the extension. Thus, a NSBL has features common to both a SBL and a NBL.

Various thermoplastic elastomers are known for use in the elastic layer, including without limitation styrenic block copolymers. For instance, U.S. Pat. No. 6,323,389 to Thomas et al. discloses the use of block copolymers having the general formula A-B-A' or A-B, wherein A and A' are each a thermoplastic polymer end block which contains a styrenic moiety such as a poly(vinylarene) and B is an elastomeric polymer midblock such as a conjugated diene or a lower alkene polymer. The A and A' blocks may be formed of the same or different polymer segments. Tetrablock copolymers having the formula A-B-A-B are also disclosed, where A is a thermoplastic polymer block as described above, and each B is an isoprene segment hydrogenated substantially to a poly(ethylene-propylene) segment.

Elastic laminates are typically the most expensive component in personal care products such as diapers, diaper pants, adult incontinence garments, feminine hygiene products and the like. Important properties of elastic laminates include providing sufficient elastic tension at various degrees of elongation during use, and providing sufficient recovery upon removal of an applied stress.

There is a need or desire for elastic laminates which perform better at lower cost.

SUMMARY OF THE INVENTION

The present invention is directed to an elastic laminate including a crosslinked elastic layer and a nonwoven web bonded to the elastic layer, wherein the elastic layer includes a styrene block copolymer ("SBC") elastomer. The crosslinked elastic layer may be a polymeric film, foam, nonwoven web or elastic strand layer. The nonwoven web may be elastic or inelastic, and may or may not be crosslinked. However, the nonwoven web is bonded to the elastic layer in such fashion that the overall laminate is elastic.

The present invention is also directed to a method of making an elastic laminate. The method includes the steps of forming an elastic layer from a thermoplastic polymer material, crosslinking the elastic layer, and bonding the elastic layer to a nonwoven web. The elastic layer may be crosslinked before or after it is bonded to the nonwoven web.

The crosslinking of the elastic layer improves the elastomeric performance of the layer, specifically the styrene block copolymer elastomer. When the uncrosslinked styrene block copolymer is a low performance elastomer, the crosslinking converts it to a high performance elastomer (or, at least, to a higher performance elastomer). When the uncrosslinked styrene block copolymer is a high performance elastomer, the crosslinking converts it to a higher performance elastomer.

The present invention permits the use of relatively less expensive lower performance elastomers as starting materials. For ease of processing, the elastic layer is formed using conditions which do not significantly crosslink the polymer materials. After the elastic layer is formed, it is crosslinked to improve its elastic performance.

With the foregoing in mind, it is a feature and advantage of the invention to provide a relatively higher performance elastic laminate, and method of making it, using relatively lower performance (and less expensive) elastic polymer materials.

DEFINITIONS

"Elastic" and "elastomeric" refer to a fiber, film or fabric which upon application of a biasing force, is stretchable by at least 50% to a stretched, biased length which is at least 50% greater than, its relaxed, unstretched length, and which will recover at least 50 percent of its elongation upon release of the stretching, biasing force.

"Recover" refers to a relaxation of a stretched material upon removal of a biasing force following stretching of the material by application of the biasing force. For example, if a material having a relaxed, unbiased length of one (1) inch was elongated 50 percent by stretching to a length of one and one half (1.5) inches the material would have a stretched length that is 50% greater than its relaxed length. If this exemplary stretched material contracted, that is recovered to a length of one and one tenth (1.1) inches after release of the biasing and stretching force, the material would have recovered 80 percent (0.4 inch) of its elongation.

"High performance elastomers" are elastomers which, when formed into a film, strand or similar article, can be extended to a stretched length and retracted without experiencing a substantial loss in retractive force at an intermediate (lower) stretched length. These elastomers typically have useful properties of high strength, low hysteresis, low creep and low permanent set. High performance elastomers have a hysteresis value of 25% or less, suitably 20% or less, determined according to the hysteresis test method described herein.

"Low performance elastomers" are elastomers which, when formed into a film, strand or similar article, can be extended to a stretched length and retracted, but substantially lose their retractive force at an intermediate (lower) stretched length. These elastomers typically exhibit higher levels of hysteresis, creep and permanent set when stretched. Low performance elastomers have a hysteresis value greater than 25%, suitably 40% or more, determined according to the hysteresis test method described herein.

"Polymer" includes homopolymers, copolymers, such as for example, block, graft, random and alternating copolymers, terpolymers, etc., and blends and modifications thereof. The term "polymer" also includes all possible geometric configurations of the molecule. These configurations include, but are not limited to, isotactic, syndiotactic and random symmetries.

"Block copolymer" is a polymer in which dissimilar polymer segments, each including a string of similar monomer units, are connected by covalent bonds. For instance, a SBS block copolymer includes a string or segment of repeating styrene units, followed by a string or segment of repeating butadiene units, followed by a second string or segment of repeating styrene units.

"Blend" refers to a mixture of two or more polymers.

"Nonwoven fabric or web" means a web having a structure of individual fibers or threads which are interlaid, but not in an identifiable manner as in a knitted or woven fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

"Spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns.

"Meltblown fibers" means fibers formed by extruding a molten thermoplastic material through a plurality of fine, usually circular, die capillaries as molten threads or filaments into converging high velocity, usually hot, gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are usually tacky when deposited onto a collecting surface.

"Microfibers" means small diameter fibers having an average diameter not greater than about 75 microns, for example, having an average diameter of from about 0.5 microns to about 50 microns, or more particularly, microfibers may have an average diameter of from about 2 microns to about 40 microns.

"Neck bonding" refers to the process wherein an elastic member is bonded to a non-elastic member while only the non-elastic member is extended or necked so as to reduce its dimension in the direction orthogonal to the extension. "Neck bonded laminate" refers to a composite elastic material made according to the neck bonding process, i.e., the layers are joined together when only the non-elastic layer is in an extended condition. Such laminates usually have cross directional stretch properties. For purposes of the invention, the elastic layers may be selected from nonwoven webs, other fibrous layers, foams, and laminates of the foregoing. Further examples of neck-bonded laminates are such as those described in U.S. Pat. Nos. 5,226,992, 4,981,747, 4,965,122 and 5,336,545 to Morman and U.S. Pat. No. 5,514,470 to Haffner et al.

"Stretch bonding" refers to a process wherein an elastic member is bonded to another member while only the elastic member is extended by at least about 50 percent of its relaxed length. "Stretch bonded laminate" refers to a composite elastic material made according to the stretch bonding process, i.e., the layers are joined together when only the elastic layer is in an extended condition so that upon relaxing the layers, the nonelastic layer is gathered. Such laminates usually have machine directional stretch properties and may be subsequently stretched to the extent that the nonelastic material gathered between the bond locations allows the elastic material to elongate. For purposes of the invention, the stretch-bonded laminate may be a stretched film laminate ("SFL") in which the elastic layer is a film. Alternatively, the elastic layer may be a nonwoven web, an array of parallel strands, another fibrous layer, or a foam or a combination of the foregoing. One type of stretch bonded laminate is disclosed, for example, by U.S. Pat. No. 4,720,415 to Vander Wielen et al., in which multiple layers of the same polymer produced from multiple banks of extruders are used. Other composite elastic materials are disclosed in U.S. Pat. No. 4,789,699 to Kieffer et al., U.S. Pat. No. 4,781,966 to Taylor and U.S. Pat. Nos. 4,657,802 and 4,652,487 to Morman and U.S. Pat. No. 4,655,760 to Morman et al., as well as U.S. Pat. No. 5,385,775 to Wright.

"Neck-stretch bonding" generally refers to a process wherein an elastic member is bonded to another member while the elastic member is extended by at least about 50 percent of its relaxed length and the other layer is a necked, non-elastic layer. "Neck-stretch bonded laminate" refers to a composite elastic material made according to the neck-stretch bonding process, i.e., the layers are joined together when both layers are in an extended condition and then allowed to relax. Such laminates usually have omni-directional stretch properties.

"Garment" means any type of non-medically oriented apparel which may be worn. This includes industrial workwear like coveralls, undergarments, pants, shirts, jackets, gloves, socks, and the like.

"Infection control product" means medically oriented items such as surgical gowns and drapes, face masks, head coverings like bouffant caps, surgical caps and hoods, footwear like shoe coverings, boot covers and slippers, wound dressings, bandages, sterilization wraps, wipers, garments like lab coats, coveralls, aprons and jackets, patient bedding, stretcher and bassinet sheets, and the like.

"Personal care product" means diapers, training pants, absorbent underpants, adult incontinence products, and feminine hygiene products.

DETAILED DESCRIPTION OF THE INVENTION

The invention is directed to an elastic laminate including a crosslinked elastic layer and a nonwoven web bonded to the elastic layer, wherein the elastic layer includes a styrene block copolymer elastomer. The term "crosslinked elastic layer" includes any such layer in which at least some of the styrene block copolymer elastomer is crosslinked, with the crosslinking occurring after the elastic layer is formed.

The styrene block copolymer elastomer used to form the elastic layer is suitably a thermoplastic elastomer which is not yet crosslinked.

Suitable styrene block copolymer elastomers include styrene-diene and styrene-olefin block copolymers. Styrene-diene block copolymers include di-block, tri-block, tetra-block and other block copolymers, and may include without limitation styrene-isoprene, styrene-butadiene, styrene-isoprene-styrene, styrene-butadiene-styrene, styrene-isoprene-styrene-isoprene, and styrene-butadiene-styrene-butadiene block copolymers. Styrene-diene polymers which include butadiene (e.g. styrene-butadiene-styrene triblock copolymers) are particularly suitable. One commercially available styrene-butadiene-styrene block copolymer is VECTOR 8508, available from Dexco Polymers L.P. Examples of styrene-isoprene-styrene copolymers include VECTOR 4111A and 4211A, available from Dexco Polymers L.P.

Styrene-olefin block polymers include without limitation styrene-diene block copolymers in which the diene groups have been totally or partially selectively hydrogenated, including without limitation styrene-(ethylene-propylene), styrene-(ethylene-butylene), styrene-(ethylene-propylene)-styrene, styrene-(ethylene-butylene)-styrene, styrene-(ethylene-propylene)-styrene-(ethylene-propylene), and styrene-(ethylene-butylene)-styrene-(ethylene-butylene) block copolymers. In the above formulas, the term "styrene" indicates a block sequence of styrene repeating units; the terms "isoprene" and "butadiene" indicate block sequences of diene units; the term "(ethylene-propylene)" indicates a block sequence of ethylene-propylene copolymer units, and the term "(ethylene-butylene)" indicates a block sequence of ethylene-butylene copolymer units. The styrene-diene or styrene-olefin block copolymer should have a styrene content of about 10 to about 50% by weight, suitably about 15 to about 25% by weight, and should have a number average molecular weight of at least about 15,000 grams/mol, suitably about 30,000 to about 120,000 grams/mol, or about 50,000-80,000 grams/mol. Styrene-diene block copolymers may be particularly advantageous for subsequent crosslinking due to the additional unsaturation.

The molecular weight of the styrene block copolymer should be low enough that the styrene block copolymer or polymer mixture can be formed into an elastic layer without inducing significant crosslinking during layer formation. The styrene block copolymer or polymer mixture should be suitable for processing at temperatures below about 220° C., suitably below about 210° C., or about 125-200° C. The molecular weight range needed to achieve this objective will vary depending on the type of styrene block copolymer, the amount and type of additional ingredients, and the characteristics of the elastic layer being formed.

The elastic layer may include at least about 25% by weight of the styrene block copolymer elastomer, or at least about 40% by weight, or at least about 50% by weight, or at least about 75% by weight. The elastic layer may include up to 100% by weight of the styrene block copolymer elastomer, or up to about 99.5% by weight, or up to about 95% by weight, or up to about 90% by weight, or up to about 80% by weight, or up to about 70% by weight. The styrene block copolymer elastomer may include one or more styrene block copolymers mixed together. Optional additional ingredients may form the balance of the elastic layer. Such ingredients include without limitation single-site catalyzed ethylene-alpha olefin copolymer elastomers having a density of less than about 0.915 grams/cm$^3$, suitably about 0.860-0.900 grams/cm$^3$, or about 0.865-0.895 grams/cm$^3$. These ethylene-alpha olefin copolymers may be formed using a $C_3$ to $C_{12}$ alpha-olefin comonomer, suitably a butene, hexene or octene comonomer. The amount of alpha olefin comonomer is about 5-25% by weight of the copolymer, suitably 10-25% by weight, and varies with the desired density. Suitable single-site catalyzed ethylene-alpha olefin copolymers are made and sold by Dow Chemical Co. under the trade names AFFINITY and ENGAGE, and by Exxon-Mobil Chemical Co., under the trade names EXACT and EXCEED.

Other optional ingredients include non-elastomeric polymers such as polyethylene, polypropylenes and other polyolefins, as well as other elastomeric polymers. When present, inelastic polymers should be employed in relatively minor amounts so as not to overcome the elastomeric characteristics of the crosslinked elastic layer.

Other optional ingredients include processing aids which assist in formation of the elastic layer at temperatures low enough to avoid significant premature crosslinking. One suitable processing aid is a polyolefin wax, for instance a branched or linear low density polyethylene wax having a density of about 0.860-0.910 grams/cm$^3$, and a melt index of about 500-4000 grams/10 min. measured using ASTM D1238 at a temperature of 190° C. and a load of 2160 grams. Examples of polyethylene waxes include EPOLENE C-10 available from the Eastman Chemical Co. and PETROTHANE NA601 available from Quantum Chemical Co. Other examples include wax-like high melt index (low molecular weight) single-site catalyzed olefin polymers available from Dow Chemical Co. under the trade name AFFINITY, for instance AFFINITY 1900 and 1950 polyolefin plastomers.

Another suitable processing aid is a styrene-based hydrocarbon tackifier having a weight average molecular weight of about 500-2500. One example is REGALREZ 1126 tackifier, available from Eastman Chemical Co. Castor oil is another suitable processing aid. Processing aids may together constitute about 0.1-50% by weight, suitably about 5-30% by weight of the elastic layer, or about 10-20% by weight of the elastic layer. When castor oil is used, it should be present in amounts suitable for crosslinking aids (indicated below).

Table 1 (below) illustrates the effect of processing aids on processing temperature in a laboratory twin-screw extrusion mixer, available from Leistritz Co. The twin screw extruder was run at constant speed (180 rpm) and constant output (2 kg/hr), at the minimum temperature suitable for mixing the ingredients and forming an elastic film layer. As shown in Table 1, the three elastomeric blends containing tackifier and polyolefin plastomer were processed at temperatures 25-50° C. lower than the remaining elastomer blends. All of the elastomeric blends could be processed at temperatures not exceeding 200° C.

TABLE 1

Processing Conditions for Various Styrenic Block Copolymers Described in this Application

| Codes | Zone 1 | Zone 2 | Zone 3 | Zone 4 | Zone 5 | Zone 6 | Zone 7 | Zone 8 | Zone 9 | Zone 10 | Zone 11 |
|---|---|---|---|---|---|---|---|---|---|---|---|
| 80% V8508 (SBS) + 10% EVA + 10% NA601 | 135 | 135 | 145 | 150 | 170 | 175 | 185 | 195 | 195 | 195 | 195 |
| 80% V8508 + 20% NA601 | 135 | 135 | 145 | 150 | 165 | 165 | 190 | 195 | 200 | 200 | 200 |
| 80% V8508 + 20% EVA | 135 | 135 | 145 | 150 | 160 | 165 | 175 | 190 | 190 | 190 | 190 |
| 80% V8508 + 20% A-PP | 135 | 135 | 145 | 150 | 170 | 175 | 185 | 195 | 195 | 195 | 195 |
| 80% V4211 (SIS) + 20% EVA | 135 | 135 | 145 | 150 | 160 | 165 | 176 | 191 | 191 | 187 | 189 |
| 80% V4111 (SIS) + 20% EVA | 135 | 135 | 145 | 150 | 180 | 185 | 185 | 190 | 190 | 190 | 190 |
| 80% V4111 + 20% NA601 | 135 | 135 | 145 | 150 | 160 | 160 | 175 | 180 | 185 | 185 | 190 |
| 80% V4111 + 10% EVA + 10% NA601 | 135 | 135 | 145 | 150 | 170 | 175 | 190 | 200 | 200 | 200 | 200 |
| 70% Experimental SBS 1 + 20% Tackifier + 10% Affinity 1900 | 145 | 145 | 145 | 150 | 150 | 160 | 160 | 165 | 165 | 165 | 165 |
| 70% Experimental SBS 2 + 20% Tackifier + 10% Affinity 1900 | 140 | 145 | 145 | 145 | 145 | 150 | 150 | 160 | 160 | 160 | 160 |
| 70% Experimental SBS 3 + 20% Tackifier + 10% Affinity 1900 | 140 | 145 | 145 | 145 | 145 | 145 | 150 | 150 | 150 | 150 | 150 |

Polymer Descriptions:
VECTOR 8508 is a styrene-butadiene-styrene triblock copolymer from Dexco Polymers LP.
VECTOR 4211 is a styrene-isoprene-styrene triblock copolymer from Dexco Polymers LP.
VECTOR 4111 is a styrene-isoprene-styrene triblock copolymer from Dexco Polymers LP.
PETROTHANE NA601 is a polyethylene wax available from Quantum Chemical Co.
EVA is ethylene vinyl acetate, Type ELVAX 3175, available from E. I. DuPont DeNemours & Co.
AFFINITY 1900 is a polyolefin plastomer available from Dow Chemical Co.
Tackifier is REGALREZ 1126, available from Eastman Chemical Co.

Other optional ingredients include crosslinking aids, i.e. additives which assist in crosslinking the formed elastic layer. One or more crosslinking aids may together constitute about 0.1-10% by weight, suitably about 0.5-5% by weight of the elastic layer. Castor oil is one such aid. Castor oil is a natural triglyceride that contains three oleic chains, each having one degree of unsaturation. Castor oil is polymerizable if subjected to an initiation source such as electron beam radiation. Castor oil is thermally stable at up to about 275° C., and can be processed in an extruder along with the styrene block copolymer elastomer without degrading. The resulting elastic layer can be polymerized (crosslinked) using a high energy radiation source, such as an electron beam. Due to the presence of three unsaturated chains on each castor oil molecule, the castor oil will assist three-dimensional crosslinking through chain transfer reactions with adjacent polymer chains.

Other crosslinking aids include without limitation multifunctional acrylate and allyl derivatives such as diethylene glycol dimethacrylate, dimethylene glycol acrylate, trimethylpropane diallyl ether, triethylene glycol dimethacrylate, and other multifunctional monomers which have adequate thermal stability in a melt extrusion process. Other crosslinking aids include polymers and oligomers having secondary carbons in a polymer backbone or side chains, as well as unsaturated double bonds. The benefits of crosslinking the elastic layers include, without limitation, a) less aging behavior, as evidenced by little or no loss in tension when the elastic layer is wound and stored on a roll, b) better temperature stability, evidenced by the ability to store and transport the elastic material without refrigeration, and c) stronger adhesion, if the elastic layer is crosslinked after lamination to the other layers.

Other optional ingredients include particulate inorganic or organic fillers. Generally, the filler particles have mean particle sizes of about 0.5-8 microns, suitably about 1-2 microns. Suitable inorganic fillers include calcium carbonate ($CaCO_3$), various kinds of clay, silica ($SiO_2$), alumina, barium sulfate, sodium carbonate, talc, magnesium sulfate, titanium dioxide, zeolites, aluminum sulfate, cellulose-type powders, diatomaceous earth, calcium oxide, magnesium oxide, aluminum hydroxide and the like. Suitable organic fillers include cellulose, cyclodextrins, and cage molecules (e.g. polyhedral oligomeric silsesquioxane nanostretched chemicals). When used, the filler particles may constitute about 20-75% by weight of the elastic film, suitably about 30-60% by weight.

The elastic layer may be in the form of a film, a foam layer, an array of strands or fibers (e.g. substantially parallel strands or fibers), a nonwoven web (e.g. a spunbond web, meltblown web, or other nonwoven web), or a combination of the foregoing. Once the elastic layer is formed, it may be crosslinked using electron-beam radiation, ultraviolet radiation, gamma radiation, or another suitable technique. The amount of radiation required will depend on the line speed, the amount of crosslinking desired, the type of radiation used and the specific composition of the elastic layer. For purposes of this invention, the elastic layer is considered to be a "crosslinked elastic layer" when its percent load loss is reduced by at least 5%, or at least 10%, or at least 20%, compared to its percent load loss prior to crosslinking, using the test procedure described below. For example, if an elastic layer demonstrates a percent load loss of 65% prior to crosslinking, then the elastic layer will be considered crosslinked if a crosslinking treatment causes its percentage load loss to fall to not more than 60% (a 5% reduction), or not more than 55% (a 10% reduction), or not more than 45% (a 20% reduction).

The nonwoven layer may be formed from a wide variety of polymers, may or may not be crosslinked, and may or may not be elastic. Suitable inelastic polymers include polyolefins such as homopolymers of ethylene, propylene and butylene, and copolymers of these monomers including up to 10% (suitably up to 5%) by weight of an alpha-olefin comonomer having up to about 12 carbon atoms. Inelastic polymers also include certain polyamides, polyesters and the like. Suitable elastic polymers include copolymers of ethylene, propylene and butylene with an alpha-olefin comonomer which generally contains more than 10% but less than 90% by weight of each comonomer. Elastic olefin copolymers include, for instance, single-site catalyzed copolymers of ethylene with more than 10% by weight of an alpha-olefin comonomer, having a density of about 0.855 to 0.900 grams/cm$^3$. Suitable elastic polymers for the nonwoven layer also include ethylene vinyl acetate, ethylene ethyl acrylate, ethylene methyl acrylate, ethylene butyl acrylate, polyurethane, block co-poly (ether-ester) and block co-poly(amide-ether).

The elastic layer and the facing layer(s) may be joined together using a variety of thermal, adhesive, ultrasonic and other processes suitable for a variety of applications. A pressure-sensitive adhesive may also be employed. A tackifier sold by Eastman Chemical Co. under the trade name REGALREZ 1126 may also serve as a pressure-sensitive adhesive. The form of the elastic layer (whether film, foam, nonwoven web, net or filament array), and the form and polymer type used in the nonwoven facing layer(s) (whether elastic or inelastic) will depend largely on the process and the end use application. Two exemplary processes for forming elastic laminates are illustrated in FIGS. 1 and 2.

Figure 1:
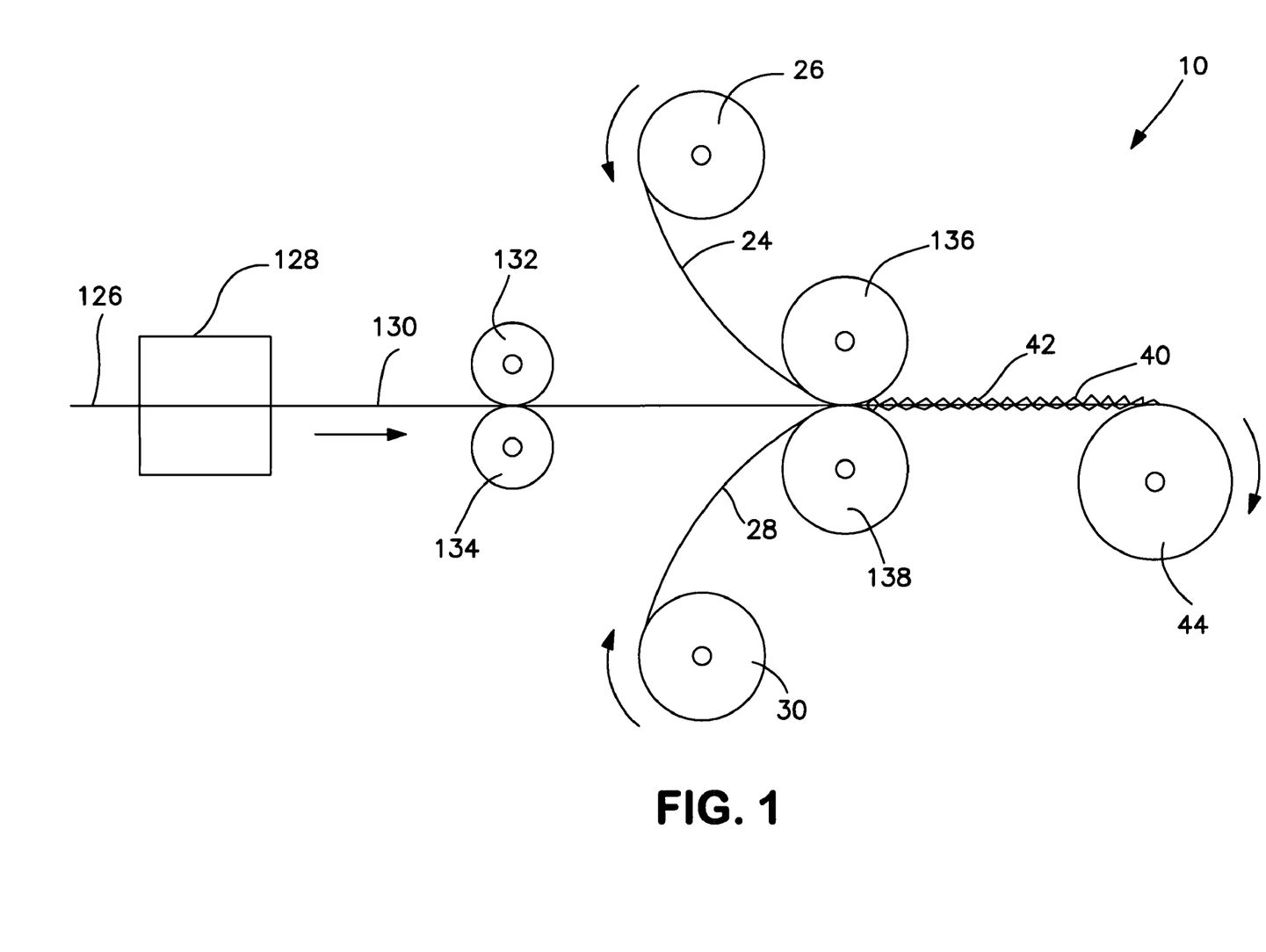
FIG. 1 schematically illustrates a process for making stretch-bonded laminates including a crosslinked elastic middle layer and two outer nonwoven facing layers.
Figure 2:
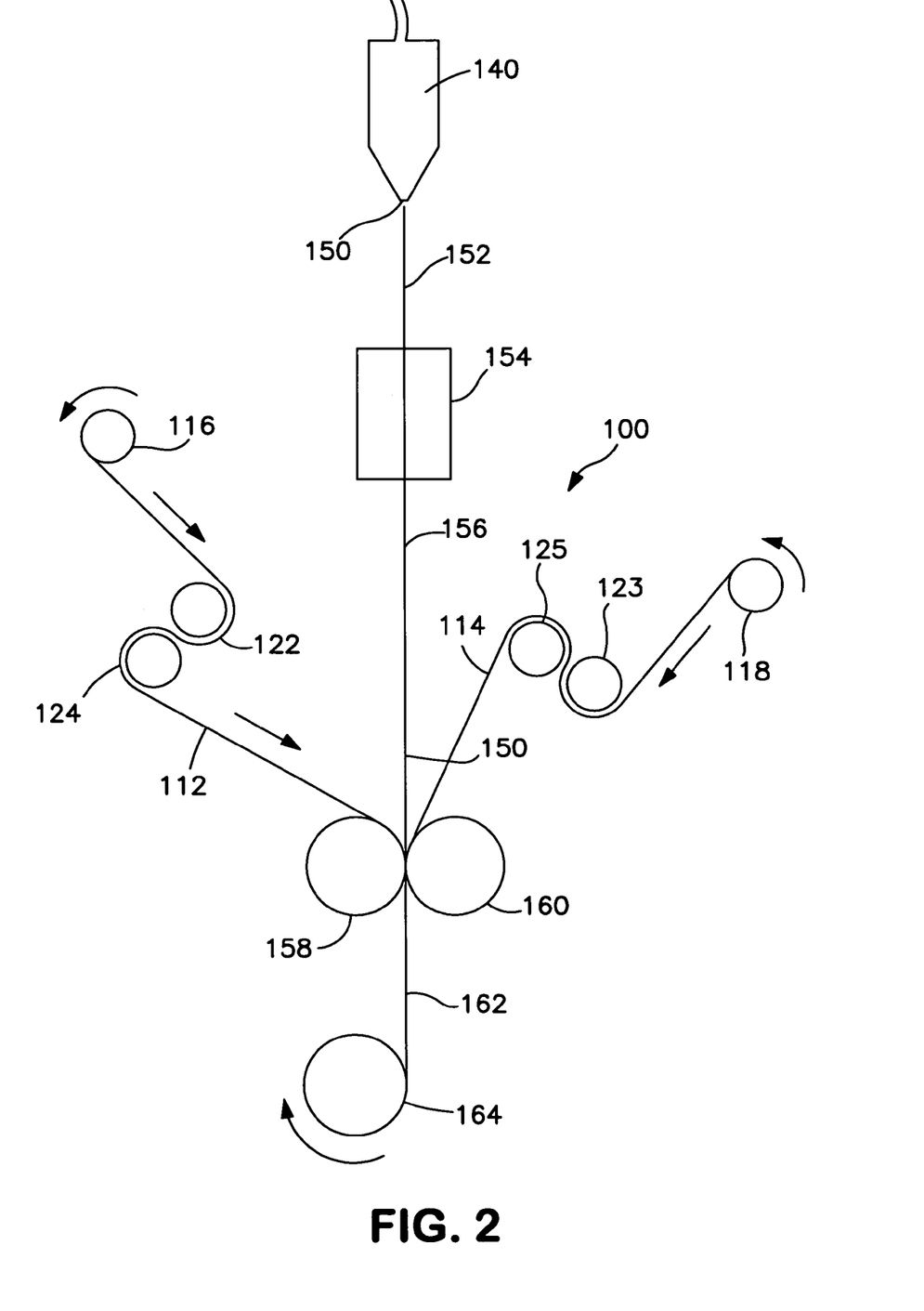
FIG. 2 schematically illustrates a process for making neck-bonded laminates including a crosslinked elastic middle layer and two outer nonwoven facing layers.

FIG. 1 schematically illustrates a process 10 for forming a stretch-bonded laminate. A thermoplastic elastic layer 126 passes a crosslinking station 128, forming a crosslinked elastic layer 130. The elastic layer can be a film, foam, fibrous nonwoven web, or elastic strand array. The crosslinking station 128, generically shown as a box, can represent a wide variety of crosslinking treatments including without limitation electron-beam radiation, ultraviolet radiation, gamma radiation or the like, alone or in combination with heat.

The crosslinked elastic layer 130 is stretched between a first set of nip rolls 132 and 134, and a second set of nip rollers 136 and 138. To cause the stretching, the second set of nip rolls turn at a surface speed at least 50% faster, suitably at least 100% faster, or 100-500% faster than the first set of nip rolls. Nonwoven facing layers 24 and 28 are unwound from storage rolls 26 and 30 and are combined with the crosslinked stretched elastic layer 130 between nip rolls 136 and 138 while the nonwoven layers 24 and 28 are relaxed. The layers may be combined with the aid of an adhesive applied to the nonwoven layers or the elastic layer, or with the aid of heat supplied from roll 136 and/or 138.

After the stretch-bonded laminate 40 is formed, the elastic layer 130 is allowed to recover and relax, resulting in striations or corrugations 42 in the nonwoven layers 24 and 28. Every time the elastic laminate 40 is stretched, the striations 42 in the nonwoven layers flatten out. The elastic laminate 40 can be stretched by at least 50% of its relaxed length, suitably by 100-700% of its relaxed length, or 150-400% of its relaxed length. When relaxed, the elastic laminate 40 will recover by at least 50% of the difference between the stretched length and the relaxed length, suitably by 75-100% of the difference. The laminate 40 can be stored on roll 44.

The crosslinked elastic layer 130 should perform as a high performance elastic layer (as defined above), regardless of whether or not the precursor (uncrosslinked) elastic layer 126 is a high performance material. The precursor elastic layer 126 may be a low performance or a high performance elastic layer, as defined above. The crosslinked elastic layer should have a lower hysteresis value than the uncrosslinked elastic layer. The difference in hysteresis between the crosslinked elastic layer and the uncrosslinked elastic layer should be at least 5%, suitably at least 10%, or at least 15%, or at least 20%, on a scale of zero to 100% hysteresis. For instance, if the crosslinked elastic layer has a hysteresis of 20% and the precursor (uncrosslinked) elastic layer has a hysteresis of 30%, then the difference in hysteresis is 10%.

The process described with respect to FIG. 1 is useful for making a stretch-bonded laminate from a crosslinked elastic layer and inelastic nonwoven facing layers. If the nonwoven facing layers were instead formed of an elastic polymer, then a suitable elastic laminate can be formed with the elastic layer in a stretched state as shown in FIG. 1, or in a relaxed state (i.e. so that all the layers are relaxed during lamination).

FIG. 2 schematically illustrates a neck-bonded laminate (NBL) process 100, in which a crosslinked elastic film is laminated between two necked nonwoven webs. A first nonwoven facing 112, which can (for example) be a polypropylene spunbond web, is unwound from a supply roll 116 and passed around a first S-wrap roll assembly including rolls 122 and 124. A second nonwoven facing 114, which can be a polypropylene spunbond web, is unwound from a supply roll 118 and passed around a second S-wrap roll assembly including rolls 123 and 125. From the S-wrap roll assemblies, the nonwoven facing layers 112 and 114 are pulled toward a bonding assembly which includes counterrotating nip rollers 158 and 160.

Nip rollers 158 and 160 turn at a surface speed which is about 1.05-1.5 times suitably about 1.1-1.4 times the surface speeds of S-wrap rolls 122, 124, 123 and 125. This causes the nonwoven layers 112 and 114 to experience high tension in the machine direction (i.e., the direction of travel), causing the nonwoven layers to elongate in the machine direction and to neck in (narrow) in the cross direction (i.e., the direction orthogonal to the machine direction). The necking in may be aided by passing each of the nonwoven layers 112 and 114 through an oven or other suitable heating device (not shown) positioned between the S-rolls 122, 124, 123, 125 and the nip rolls 158, 160. The S-rolls and/or nip rolls may also be suitably heated. For polypropylene spunbond webs, suitable necking temperatures may range from about 220-280° F. Each nonwoven layer 112, 114 can be necked to about 25-80% of its initial width, suitably to about 30-70% of its initial width.

An elastic polymer mixture can be heated and blended in an apparatus 140 and extruded through a slot die 150 in the form of a molten elastic film 152. The molten elastic film 152 is passed through a crosslinking station 154 to form a crosslinked elastic film 156. The crosslinked elastic film 156, which may still be warm and tacky, is passed between the nip rolls 158 and 160, to cause bonding between the film and the necked nonwoven layers. The bonding may be aided with an adhesive applied to the film or nonwoven layers. The resulting neck-bonded laminate 162 has elastic stretch and recovery properties in the cross-direction. Stretching of the laminate 162 in the cross direction causes the nonwoven layers 112 and 114 to become un-necked, and relaxation of the stretched laminate causes the nonwoven layers to become necked again. The neck-bonded laminate 162 can be wound and stored on roll 164, or it can be conveyed for further processing and use.

A variation of the NBL process is the neck-stretch bonded laminate (NSBL) process. In such a process, the elastic film 152 shown in FIG. 2 would be cooled and crosslinked, then stretched in the machine direction before being bonded to the necked nonwoven layers 112 and 114. A laminate formed by a NSBL process has elastic stretch and recovery properties in both the machine and cross directions. Furthermore, in the NSBL process, the elastic film 152 can be replaced with an elastic fibrous nonwoven web, an elastic foam, an elastic net or strand array, or an elastic laminate. The layers can be bonded together by adhesive or thermal bonding and pressure applied between the nip rolls 158 and 160.

In another variation of any of the foregoing processes, the elastic layer may be crosslinked after it is laminated to the nonwoven facing layer(s), instead of before. If the crosslinking occurs after lamination, radiation of somewhat higher intensity may be required to pass through the nonwoven layer(s) and crosslink the elastic film. Also, the elastic film (before or after combination with the nonwoven layer(s)) may be irradiated from one or both sides.

The elastic laminates can be used in a wide variety of disposable articles, including without limitation garments, infection control products, and personal care products as defined above. The elastic laminates perform as high performance elastic materials in these applications and have hysteresis values less than 25%, suitably less than 20%, or less than 15%.

EXAMPLE

A continuous filament stretch-bonded laminate ("CFSBL") was prepared by first spinning an array of substantially continuous parallel elastic strands from a vertical extrusion die onto a chill roll. The die was fed by a twin screw extruder. The elastic polymer, identified as KRATON D1117 available from Kraton Polymers LLC, was processed at a melt temperature of 162° C. This elastic polymer contains about 60% by weight styrene-isoprene-styrene triblock copolymer, and about 40% by weight styrene-isoprene diblock copolymer.

For the six samples listed below, the elastic strand composition included 83% by weight KRATON D1117, 10% by weight REGALREZ 1126 tackifier available from Eastman Chemical Co., and 7% by weight EPOLENE C-10 wax available from Eastman Chemical Co. The quenched elastic strands were stretched to 5-6 times their original length and were laminated between two polypropylene spunbond facing layers, each having a basis weight of 13-14 gsm, by passing the layers between opposing smooth nip rolls. To aid in the lamination, each spunbond layer was previously sprayed with about 2.5 gsm of Findley H2840 adhesive available from Bostik-Findley, Inc. The resulting laminate was relaxed and wound on a roll. Without crosslinking the elastic strand layer, the laminate was tested for load loss using the procedure below, and experienced a load loss of 65% at body temperature (37° C.) after 12 hours.

Samples of the CF-SBL were then exposed to electron-beam radiation at 5, 10, 15, 20 and 25 mega-rads, as indicated below. As shown in the table below, the resulting crosslinking of the elastic strand layer resulted in generally lower load losses for the laminate samples.

TABLE 2

Load Loss vs. Radiation Exposure

| Sample | Radiation (Mrads) | % Load Loss (12 hrs, 37° C.) |
|---|---|---|
| 1 | 0 | 67 |
| 2 | 5 | 43 |
| 3 | 10 | 29 |
| 4 | 15 | 38 |
| 5 | 20 | 47 |
| 6 | 25 | 29 |

Test Procedures

Test For Measuring Hysteresis

The hysteresis of an elastic material is determined using a Sintech 1/S or 2/S apparatus equipped with TESTWORKS software to record data. The elastomeric material is cut into strips, each having a width of three inches and a length of six inches. Both ends of the material are clamped into the opposing jaws of the apparatus, so that one inch of the length on each end of the material is maintained within the jaws and four inches of the length are available for stretching.

Each material strip is stretched at a rate of 500 mm/min by 100% (increasing the exposed length from 4 to 8 inches) and the area under the curve (representing force X displacement) is measured and recorded as the "loading energy." The material strip is then allowed to recover to a length where the stretching force is zero. During retraction, the area under the curve is again measured and recorded. This is the "unloading energy."

Hysteresis is determined according to the following equation:

$$\% \text{ Hysteresis} = \left[ \frac{\text{loading energy minus unloading energy}}{\text{loading energy}} \right] \times 100\%$$

Procedure for Determining Load Loss (% LL) and Slope

The load loss (% LL) and slope are determined using a stress relaxation experiment with a one-inch wide by seven-inch long strip of elastic material. The ends of the strip are clamped into a Sintech 1/S or 2/S frame equipped with TESTWORKS software to record data. Two inches of the strip length are maintained within the clamping jaws on both ends, and three inches of the length are exposed.

The testing apparatus is maintained in a 100° F. controlled temperature chamber. The film strip is stretched at a rate of 40 inches per minute to an elongation of 50%, and is maintained in the stretched condition for twelve hours. The load as a function of time is measured and plotted, typically yielding a curve which shows exponential load loss.

The load loss (% LL) over time (t) is determined from the following equation:

$$\% \ LL = \frac{\text{Load}(t=0) \text{minus Load}(t=12 \text{ hours})}{\text{Load}(t=0)} \times 100\%$$

where
  t=time, hours

The slope, which is constant over the time period, is determined from a plot of log (load) versus log (time), or from the following equation:

$$m = \frac{-\log[(L(t)/L(0)]}{\log t}$$

where
  m=slope,
  L(t)=load at a given time (t),
  L(0)=starting load at t=0, and
  t=time Once the load loss and slope have been determined, the load L at any given time T can be determined from the following equation:

$$L(t) = L(0) t^{-m}$$

where m=magnitude (absolute value) of slope of line,
  t=time,
  L(t)=load at a given time, and
  L(0)=starting load at t=0

While the embodiments of the invention disclosed herein are exemplary, various modifications and improvements can be made without departing from the spirit and scope of the invention. The scope of the invention is indicated by the appended claims, and all changes that fall within the meaning and range of equivalents are intended to be embraced therein.

We claim:

1. An elastic laminate, comprising:
a crosslinked elastic layer including a styrene block copolymer elastomer constituting 75-100% by weight of the crosslinked elastic layer, a processing aid, and a crosslinking aid, the processing aid being configured to inhibit significant crosslinking prior to the formation of the elastic layer, wherein a percent load loss of the crosslinked elastic layer is reduced by at least 5% compared to a percent load loss prior to crosslinking of the elastic layer; and
a nonwoven web bonded to the crosslinked elastic layer.

2. The elastic laminate of claim 1, wherein the styrene block copolymer elastomer comprises a styrene-diene block copolymer selected from the group consisting of styrene-isoprene, styrene-butadiene, styrene-isoprene-styrene, styrene-butadiene-styrene, styrene-isoprene-styrene-isoprene, and styrene-butadiene-styrene-butadiene block copolymers, and combinations thereof.

3. The elastic laminate of claim 2, wherein the styrene block copolymer further comprises a styrene-olefin block copolymer.

4. The elastic laminate of claim 1, wherein the crosslinking aid comprises castor oil.

5. The elastic laminate of claim 1, wherein the crosslinking aid comprises a multifunctional acrylate or allyl derivative.

6. The elastic laminate of claim 1, wherein the crosslinking aid comprises a polymer having secondary carbon atoms and unsaturated double bonds.

7. The elastic laminate of claim 1, wherein the crosslinked elastic layer further comprises an additional elastomer.

8. The elastic laminate of claim 1, wherein the processing aid comprises a polyolefin wax.

9. The elastic laminate of claim 1, wherein the processing aid comprises a single-site catalyzed polyolefin plastomer.

10. The elastic laminate of claim 1, wherein the processing aid comprises a styrene-based hydrocarbon tackifier.

11. The elastic laminate of claim 1, wherein the crosslinked elastic layer further comprises a polyolefin.

12. The elastic laminate of claim 1, wherein the crosslinked elastic layer comprises a particulate filler.

13. The elastic laminate of claim 1, further comprising an additional nonwoven web bonded to the crosslinked elastic layer.

14. An elastic laminate, comprising:
a crosslinked elastic layer including 75-100% by weight of a styrene-diene block copolymer elastomer, a processing aid, and a crosslinking aid, the processing aid being configured to inhibit significant crosslinking prior to the formation of the elastic layer, wherein a percent load loss of the crosslinked elastic layer is reduced by at least 5% compared to a percent load loss prior to crosslinking of the elastic layer;
a first nonwoven web bonded to a first side of the crosslinked elastic layer; and
a second nonwoven web bonded to a second side of the crosslinked elastic layer.

15. The elastic laminate of claim 14, wherein the crosslinked elastic layer comprises a film.

16. The elastic laminate of claim 14, wherein the crosslinked elastic layer comprises a foam.

17. The elastic laminate of claim 14, wherein the crosslinked elastic layer comprises an array of substantially parallel strands.

18. The elastic laminate of claim 14, wherein the crosslinked elastic layer comprises a nonwoven web.

19. The elastic laminate of claim 14, wherein the laminate is a stretch-bonded laminate.

20. The elastic laminate of claim 14, wherein the laminate is a neck-bonded laminate.

21. The elastic laminate of claim 14, wherein the laminate is a neck-stretch-bonded laminate.

22. The elastic laminate of claim 12, wherein the particulate filler constitutes 20-25% by weight of the crosslinked elastic layer.

23. The elastic laminate of claim 1, wherein the nonwoven web is crosslinked.

24. The laminate of claim 1, wherein the nonwoven web is not crosslinked.

25. The laminate of claim 1 wherein the nonwoven web comprises a polyolefin.

26. The laminate of claim 1, wherein the nonwoven web comprises a polyester or polyamide.

27. The laminate of claim 1, wherein the nonwoven web comprises an elastic polymer.

28. The laminate of claim 1, wherein the crosslinked elastic layer is a high performance elastic layer.

29. The laminate of claim 14, wherein the crosslinked elastic layer is a high performance elastic layer.

30. The laminate of claim 14, wherein at least one of the nonwoven webs is crosslinked.

31. The laminate of claim 14, wherein each of the nonwoven webs comprises a polyolefin, polyamide or polyester.

* * * * *